United States Patent [19]
Arenberg et al.

[11] 4,175,563
[45] Nov. 27, 1979

[54] BIOLOGICAL DRAINAGE SHUNT

[76] Inventors: Irving K. Arenberg, 6209 S. Highlands, Madison, Wis. 53705; John B. Newkirk, 24400 Snow Valley Rd., Evergreen, Colo. 80439

[21] Appl. No.: 839,405

[22] Filed: Oct. 5, 1977

[51] Int. Cl.² .................................... A61M 27/00
[52] U.S. Cl. ........................ 128/350 V; 128/274
[58] Field of Search ............ 128/348, 350 R, 350 V, 128/274, 1 R

[56] References Cited
U.S. PATENT DOCUMENTS

| | | | |
|---|---|---|---|
| 3,654,932 | 4/1972 | Newkirk et al. | 128/350 V |
| 3,788,327 | 1/1974 | Donowitz et al. | 128/350 R |
| 4,037,604 | 7/1977 | Newkirk | 128/350 V |

Primary Examiner—Dalton L. Truluck
Attorney, Agent, or Firm—Richard D. Law

[57] ABSTRACT

A body fluid drainage apparatus or shunt for implantation in the inner ear or elsewhere includes an essentially rigid elongated tube having one open end and a closed, flexible end with a valve, a generally rigid housing fixedly secured to and telescoping over the closed end of said elongated tube, a pair of angularly, oppositely extending arms fixedly secured to the assembly, and a pair of plastic films, with open sides, secured to the apparatus enclosing the valve. When the valve is a slit valve, it is sealed in a flexible tube sealed to and extending a short distance beyond the elongated tube.

11 Claims, 7 Drawing Figures

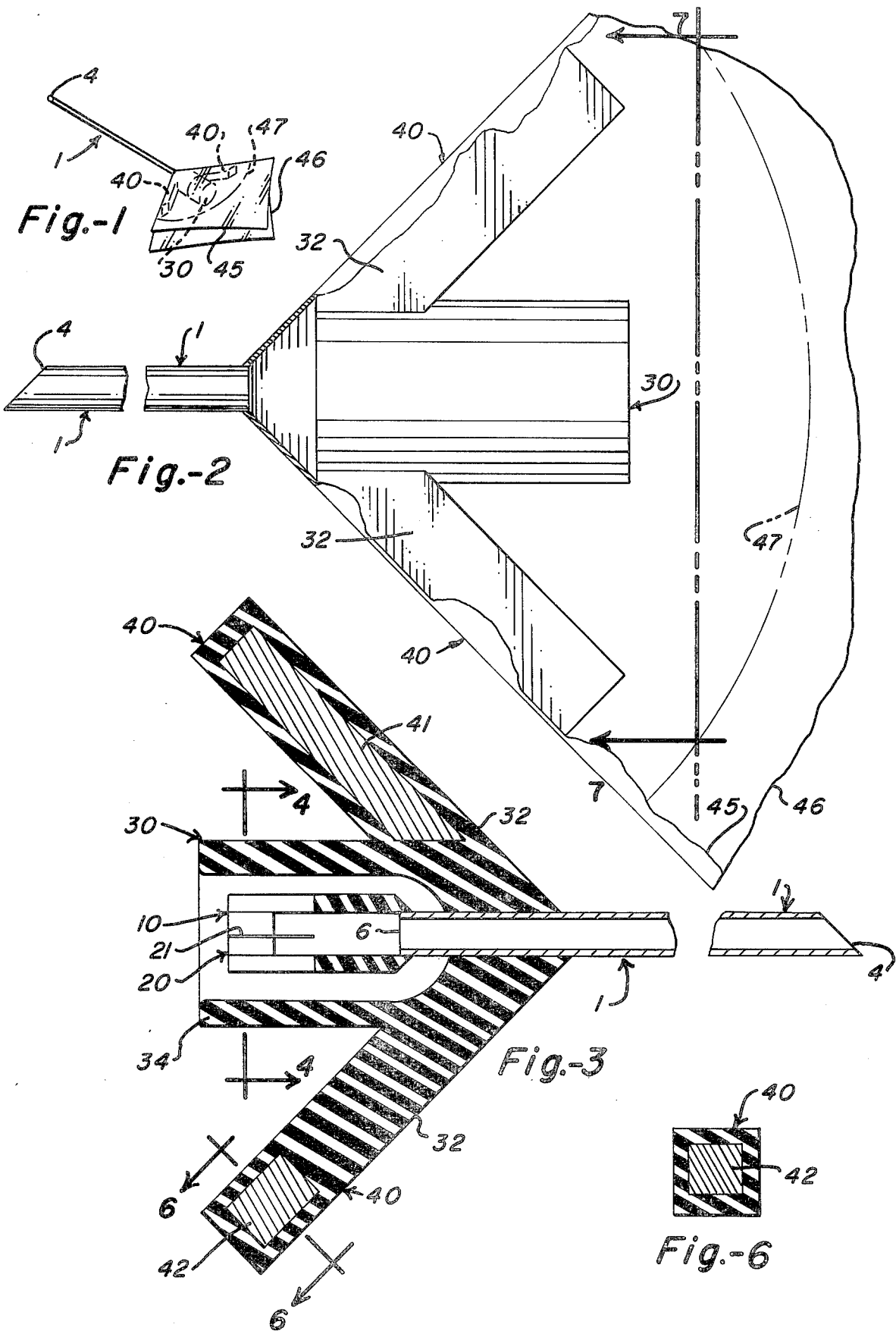

BIOLOGICAL DRAINAGE SHUNT

BACKGROUND OF THE INVENTION

This invention relates to a shunt for fluid drainage out of the inner ear. Otologic problems include, among many others, Meniere's disease of either the "classic" type, the cochlear type (cochlear hydrops), the vestibular tupe (vestibular hydrops) or fluctuant hearing loss. Cochlear Meniere's disease may be frequently misdiagnosed as a middle ear pressure problem related to episodic Eustachian tube dysfunction. The increased, fluid volume and pressure resulting from the disease may be relieved by implanting a one way valved shunt. One method of alleviating the inner ear fluid volume excess which builds up, is to implant a shunt which directs the excess endolymph out of the endolymphatic system through the endolymphatic sac, draining fluid therefrom. This converts the closed inner ear fluid system to an open inner fluid system with long term drainage.

Various drainage devices have been made for various purposes. These are called shunts and sometimes include a valve. In U.S. Pat. No. 3,654,932, issued Apr. 11, 1972, there is described a hydrocephalus shunt which includes a pump. This is included in a long tube extending from the ventricular cavity to the vascular system or elsewhere. A similar type shunt is shown in U.S. Pat. No. 2,969,066, for a similar purpose.

Small shunts have been devised for implantation in the eye for control of glaucoma. Ness U.S. Pat. No. 3,159,161, shows an open shunt of a general "L" shape to permit relief of liquid under pressure from the eye. Donowitz U.S. Pat. No. 3,788,237, uses a straight tube with leaf valve centrally of the tube for eye implantation. Newkirk U.S. Pat. No. 4,037,604, uses a straight tube with cross-slit valve similar to the valve used in the present invention.

SUMMARY OF THE INVENTION

According to the present invention, we have conceived and developed a body fluid drainage apparatus or shunt for implantation into the inner ear, (specifically the endolymphatic sac). This unit comprises an elongated tube having one open end and a closed end with a valve. An outer generally cylindrical essentially rigid tubular housing is fixedly secured to the elongated tube and the housing and extends toward the valve end. The valve is formed of a generally cylindrical solid plug or membrane in fluid-tight engagement with the extension tube, with the plug having at least one slit therethrough. A pair of flaps cover the valve end permitting free flow of liquid from the valve. In one form, radiographic opaqueness is provided on the unit since it is implanted in a closed environment.

OBJECTS OF THE INVENTION

Among the objects and advantages of the invention is to provide an inner ear fluid shunt.

Another object of the invention is to provide an inner ear fluid shunt with a slit valve, and further provide a housing for protection of the valve.

Still another object of the invention is to provide an inner ear fluid shunt arranged with valve covering flaps for maintaining an open inner ear fluid system.

Yet another object of the invention is to provide a shunt for implantation in an inner ear which is compatible with its implanted environment and will not migrate when in use.

An additional object of the invention is to provide a shunt which is sizable by the surgeon to fit the particular patient's surgical anatomic situation.

A still additional object of the invention is to provide an inner ear fluid shunt having protective means for a slit valve in the shunt.

Yet another object of the invention is to provide a valved shunt for implantation in human tissue provided with a larger perimeter drainage area.

These and other objects of the invention may be readily ascertained by reference to the appended drawings and the accompanying description, in which:

GENERAL DESCRIPTION OF THE DRAWINGS

FIG. 1 is a slightly enlarged oblique view of one form of the invention.

FIG. 2 is an enlarged top plan view of one form of the invention.

FIG. 3 is an enlarged top plan cross-sectional view of the valve and shunt portion of the device of the invention.

FIG. 6 is a cross-sectional view of an extending arm of the unit taken along section lines 6—6 of FIG. 3.

SPECIFIC DESCRIPTION OF THE DRAWINGS

Figure 4:
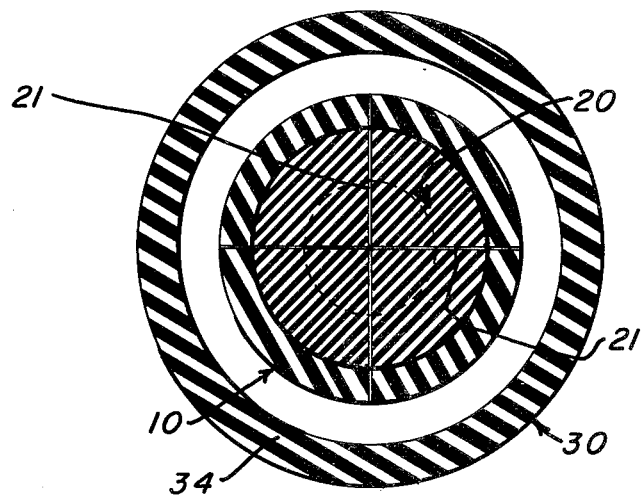
FIG. 4 is an enlarged cross-sectional view of the valve and housing portions taken along view lines 4—4 of FIG. 3.

One form of the body liquid drainage shunt, of the present invention, is shown in FIGS. 1-6, and it generally comprises an elongated, essentially rigid tube 1, a flexible extension tube 10, a slit valve 20, generally an essentially rigid, tubular housing 30, and a pair of angularly extending oppositely directed arms 40 which may or may not be integrally a part of the extension tube 10. The elongated tube 1 has a diagonally cut, open end 4 and a squared, open end 6. A generally tubular housing 30 is provided around the squared, open end portion annularly encompassing the flexible tube 10. Inwardly converging conical surfaces 32 connect one end of the housing to the tube 1, and maintains the generally tubular body 34, of the housing, a spaced uniform distance therefrom. The housing has a cylindrical bore therein, which is open to one end thereof and closed by its connection to tube 1 at the inner surface of conical surface 32. Extending oppositely, and at an angle outwardly, from the tube 1 and housing 30 are a pair of arms 40. These arms may be rectangular or circular or otherwise in cross section and form about a 90° angle at the intersection. Thus, each extends outwardly at about a 45° angle from the tube axis.

The tube 1 is, preferably, made of Supramid (TM), a synthetic plastic, which is reasonably rigid so as to maintain its geometric configuration in the implant environment. This tube is made at least 5 mm long so it may be cut to desired length, by the surgeon, for the particular patient. The arms 40 and the housing are made of molded medical grade silicone rubber, which has a durometer to be biocompatibly soft yet maintain its geometric configuration under implant conditions. This condition is to provide mechanical protection of the tube 10 from pressure by the surrounding tissue, which may have a tendency to bear against the flexible tube or plug, changing the pressure-flow characteristics of the slit valve 20. The flexible tube 10 is a soft, medical grade silicone rubber tube, and the plug or membrane, also, is a soft silicone rubber. The combination of the tube and membrane permits the slit valve to operate in a predetermined fashion. The flow rate and/or operating pressure is generally controlled by the valve, taking into effect the (a) stiffness of the rubber; (b) diameter of the tube; (c) thickness of the membrane; (d) length and number of slits in the membrane and tube wall at the plug.

Figure 5:
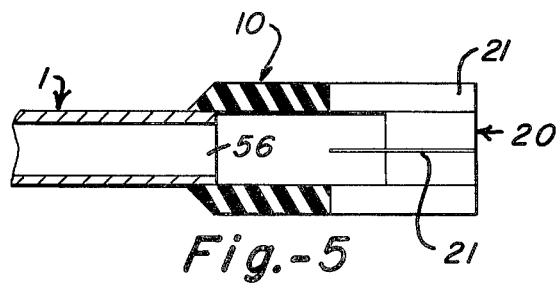
FIG. 5 is an enlarged detail view of one form of the valve of the invention.
Figure 7:
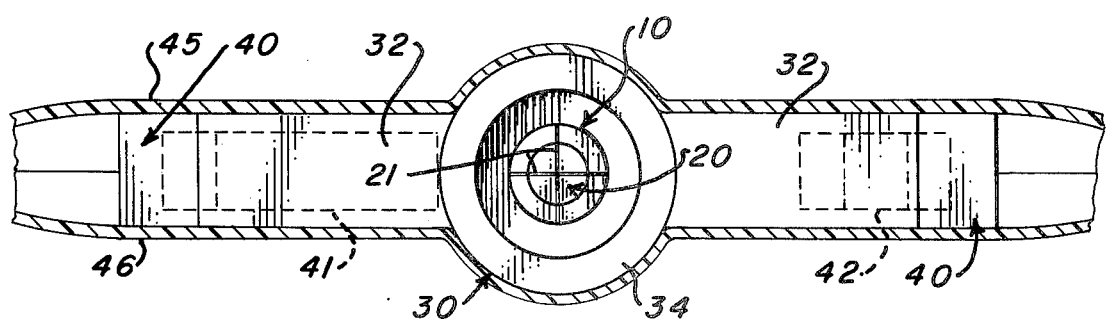
FIG. 7 is an enlarged end view of the device taken along section lines 7—7 of FIG. 2.

The soft flexible resilient extension tube 10 telescopically extends over and is sealed to the squared end of elongated tube 1. The other end of the extension tube 10 is provided with plug 20, having at least one slit 21, in fluid-tight and sealed engagement therewith. FIGS. 4 and 5 illustrate crossed slits in the plug and tube. The slit valve, which includes the generally cylindrical solid plug having at least one slit therethrough, acts as a valve for body liquids flowing through elongated tube 1 and extension tube 10. The slit or slits must extend through the plug and into the wall of the tube. At a predetermined pressure exerted by the body liquids in the flexible tube 10, the valve will be forced open, thereby allowing a flow of liquids therethrough. The pressure necessary to open the slit valve to liquid flow is dependent on the several factors enumerated above.

In particular, the shunt of the present invention is adapted to be implanted in the ear, so as to drain liquid contained in the inner ear to a suitable body site. Therefore, the shunt must be constructed of stable materials which are inert or innocuous to all of the tissues and liquids of the ear. Further, the unit must be sized so as to conform to the dimensions of the inner ear and its environs. In one embodiment, the elongated tube is approximately a 7 mm length of "Supramid" (T.M.) tubing. The generally cylindrical housing has approximately a 1½ mm square cross section. It is obvious that the small size indicates microsurgery, usually conducted under an operating microscope or magnifying lenses.

In a preferred embodiment, the shunt of the present invention is provided with a pair of superimposed, generally rectangular flaps 45 and 46. The flaps are fixedly secured to the housing 30 and both of the arms 40 by any suitable means, such as, for example, by biocompatible adhesive or cement. The pair of flaps may be integrally formed together at the point of attachment to the housing and arms or the flaps may be fixedly secured to one another, but the distal edges are not secured together. The pair of flaps are dimensioned so as to be capable of being sized (as by cutting) to fit any human ear as along cut line 47. The pair of flaps may be made from any suitable material such as, for example, a sheet or film of medical grade silicone rubber. The film flaps are flexible and thin. The two flaps form a protection over the end of the housing and the valve, and they, with the rigid sidearms, create a fluid filled space, including the valve mechanism, so as to have a fluid interface to facilitate inner ear fluid exchange or transfer with the external milieau and to prevent intrusion of tissue onto the valve, thereby disrupting its predetermined pressure and liquid flow characteristics. These valves are prepared, individually tested for their pressure and/or flow characteristics and labeled. The surgeon may then choose the valve having those characteristics believed desirable for the particular patient. The flaps, also, provide a large area drainage perimeter extending outwardly from the valve for the flow of liquid from the valve to the absorbing site. The probability of converting the closed inner ear fluid system to an open inner ear fluid system is facilitated by these flaps which can promote a long term inner ear fistula.

As implanted in the ear, the flaps, therefore, serve to prevent body tissue and fluids from impinging on the slit valve and thereby preventing proper functioning of the valve. Further, the generally tubular housing, also, prevents body tissue or body fluid from pressing on the outside on the extension tube thereby causing dysfunction of the slit valve.

Although a preferred embodiment was aforedescribed with respect to dimensions and materials employed in the construction thereof, a number of suitable materials are available to comply with the medical and engineering specifications of the shunt. Further, although the shunt of the present invention has been illustrated with two crossed slits therethrough, it may possess a single slit or more than two slits. The slits may be of a length or lengths into the tube 10 to produce the desired predetermined flow rate at a given applied pressure which length(s) will be dependent on all the factors aforedescribed. The length of the shunt may be determined by the surgeon in view of the exact problems of the patient to be rectified and the specific body dimensions encountered therein.

The shunt is implanted in the inner ear and is not readily visible by visual examination. For radiographic examination, material which strongly absorbs X-rays, etc. may be placed in or on the arms or housing as may be desired. Gold, tantalum or other heavy element strips, bars or paint may be placed on or imbedded within the arms. For example, a strip 41 is placed on one arm 40 and a shorter strip 42 is placed on the other. This provides means for ascertaining the location and the orientation of the device. The opaque material must be isolated from or be innocuous to the biological tissue at site of the implant, thus, the metals listed (among other materials) may be used. When added by painting, silicone rubber film may cover the material. Strips, bars, etc. of the material may also be embedded in the material on the arms, or any other part of the described invention which will further facilitate radiographic evaluation and orientation of the implant by radiographic means.

While inventive concepts have been disclosed herein in reference to a presently preferred and illustrative embodiment of the invention, it is contemplated that those concepts may be variously employed and embodied in alternate structure. It is intended that the appended claims be construed to cover alternate embodiments of the inventive concepts except insofar as precluded by the prior art.

What is claimed is:

1. A body fluid drainage apparatus such as an inner ear shunt, comprising:
    (a) an elongated tube composed of a material which will maintain its shape on being implanted and having two open ends;
    (b) a flexible extension tube fixedly secured to and telescoping over one end of said elongated tube;
    (c) a soft resilient closure means in the opposite end of said flexible tube and having at least one valve therein;
    (d) an outer generally cylindrical housing fixedly secured to said elongated tube and having a cylindrical bore therein which generally encompasses a portion of said elongated tube and said extension tube;

(e) a pair of radially, oppositely extending arms fixedly secured to said elongated tube and said housing; and (f) a pair of superposed, generally rectangular thin, flexible, resilient flaps fixedly secured to said housing and said arms encompassing said flexible extension tube and said closure to prevent tissue form impinging thereon.

2. The apparatus of claim 1 where said soft resilient closure is a plug in the end of said flexible tube.

3. The apparatus of claim 1 wherein said pair of arms are generally rectangular or circular in cross section.

4. The apparatus of claim 1 wherein said closure means and said at least one valve comprises a generally cylindrical solid plug in fluid-tight engagement with said extension tube and having at least one slit therethrough.

5. The apparatus of claim 4, wherein said cylindrical plug has a pair of cross slits therethrough.

6. The apparatus of claim 1 wherein said flaps are generally square and larger than necessary for implant and are arranged to be cut to the necessary size and shape for each implant.

7. The apparatus of claim 6, wherein said flaps are made of silicone rubber film.

8. The apparatus of claim 1 wherein the elements are made of an inert and innocuous material with respect to body tissue and fluids.

9. The apparatus of claim 8 wherein said housing, pair of arms, and said extension tube are integral, and said valve are all made from a medical grade silicone rubber.

10. The apparatus of claim 8 where said elongated tube is made from an essentially rigid biocompatible plastic.

11. The apparatus of claim 8 where said elongated tube is a biocompatible metal.

* * * * *